(12) United States Patent
Baek et al.

(10) Patent No.: US 10,105,111 B2
(45) Date of Patent: Oct. 23, 2018

(54) PET-RFA COMPLEX MEDICAL DEVICE AND TREATMENT METHOD USING THE SAME

(71) Applicant: UNIVERSITY-INDUSTRY FOUNDATION (UIF), Seoul (KR)

(72) Inventors: Jong Duk Baek, Incheon (KR); Shin Kook Choi, Seoul (KR); Gi Hun Kim, Incheon (KR); Min Ah Han, Seoul (KR)

(73) Assignee: UNIVERSITY-INDUSTRY FOUNDATION (UIF) (KR)

( * ) Notice: Subject to any disclaimer, the term of this patent is extended or adjusted under 35 U.S.C. 154(b) by 1120 days.

(21) Appl. No.: 14/250,993

(22) Filed: Apr. 11, 2014

(65) Prior Publication Data
US 2014/0330264 A1    Nov. 6, 2014

(30) Foreign Application Priority Data
May 3, 2013    (KR) .................. 10-2013-0050092

(51) Int. Cl.
 A61B 18/18    (2006.01)
 A61B 6/03    (2006.01)
 A61N 1/40    (2006.01)
 A61B 18/00    (2006.01)

(52) U.S. Cl.
 CPC .............. *A61B 6/037* (2013.01); *A61N 1/403* (2013.01); *A61B 2018/00577* (2013.01); *A61B 2018/1807* (2013.01)

(58) Field of Classification Search
 CPC .......... A61B 18/18; A61B 2018/00577; A61B 2018/1807; A61B 6/037; A61N 1/403
 See application file for complete search history.

(56) References Cited

U.S. PATENT DOCUMENTS

| 2006/0161246 | A1 | 7/2006 | Rhim et al. |
| 2008/0033420 | A1 | 2/2008 | Nields et al. |
| 2011/0054304 | A1 | 3/2011 | Markowitz et al. |
| 2012/0226091 | A1 | 9/2012 | Mishelevich |
| 2013/0158382 | A1* | 6/2013 | Chao .................. A61N 5/1082 600/407 |
| 2014/0303616 | A1 | 10/2014 | Shin et al. |

FOREIGN PATENT DOCUMENTS

| JP | 4374345 | 4/2006 |
| KR | 20080105442 | 12/2008 |
| KR | 101248959 | 11/2012 |
| WO | 2011/021412 | 2/2011 |

OTHER PUBLICATIONS

Notice of Allowance dated Oct. 30, 2014 for Korean Patent application No. 10-2013-0050092, with an English translation.

* cited by examiner

*Primary Examiner* — Michael Peffley
*Assistant Examiner* — Samantha Good
(74) *Attorney, Agent, or Firm* — Onello & Mello, LLP.

(57) ABSTRACT

Provided are a positron emission tomography (PET)-radiofrequency ablation (RFA) complex medical device and a treatment method using the same. According to an aspect of the present invention, there is provided a positron emission tomography (PET)-radiofrequency ablation (RFA) complex medical device comprising: a PET module which obtains, in real time, a location of a target to be treated by scanning a patient; and an RFA module which remotely treats the target using heat by focusing the heat on the location of the target.

7 Claims, 3 Drawing Sheets

PET-RFA COMPLEX MEDICAL DEVICE AND TREATMENT METHOD USING THE SAME

CROSS REFERENCE TO RELATED APPLICATIONS

This application claims priority from Korean Patent Application No. 10-2013-0050092, entitled PET-RFA COMPLEX MEDICAL DEVICE AND TREATMENT METHOD USING THE SAME, filed on May 3, 2013 in the Korean Intellectual Property Office, the disclosure of which is incorporated herein by reference in its entirety.

BACKGROUND OF THE INVENTION

1. Field of the Invention

The present invention relates to a positron emission tomography (PET)-radiofrequency ablation (RFA) complex medical device and a treatment method using the same, and more particularly, to a PET-RFA complex medical device which simultaneously performs the monitoring and thermotherapy of a target, that is, obtains, in real time, location information of a target to be treated by using PET and treats the target using heat by focusing the heat on the target using RFA instead of inserting an electrode into the target, and a treatment method using the PET-RFA complex medical device.

2. Description of the Related Art

Currently, radiation therapy is being widely used for cancer diagnosis and treatment. However, radiation therapy adversely affects patients due to a large amount of radiation exposure. For example, radiation can cause DNA changes, cancer, nausea, headaches, etc. depending on the radiation dose.

Therefore, international efforts are being made to reduce the amount of radiation exposure that patients will receive. For example, treatments for liver cancer include liver transplantation, liver resection, percutaneous alcohol injection, and radiofrequency ablation (RFA). In particular, RFA is a method of treating a cancer cell without surgery by generating radiofrequency waves and burning the cancer cell with heat generated from the radiofrequency waves.

FIG. 1 is a diagram illustrating cancer detection using conventional positron emission tomography (PET). FIG. 2 is a diagram illustrating cancer treatment using conventional RFA.

Referring to FIG. 1, PET is a method of capturing an image of metabolic processes to diagnose any problem with metabolism. In PET, a medicine combined with a radioactive isotope that emits positrons is injected into a human body P as indicated by reference numeral 11. Then, the medicine is traced using a detector 12 to identify the distribution of the medicine within the body P. A PET device has high specificity and sensitivity to cancer. However, PET uses radiation during a scan time for obtaining cancer information (e.g., location, size, etc.). Radiation is also used during radiation therapy for curing cancer detected by PET.

Referring to FIG. 2, RFA is a method of removing a cancer cell 5 by inserting an electrode 21 into human tissue T, generating radiofrequency waves from the electrode 21, and burning the cancer cell 5 with heat 22 generated from the radiofrequency waves. In RFA, the electrode 21 is inserted into a region around the cancer cell 5, and then the cancer cell 5 is heated. Therefore, RFA is a limited method depending on a body part and carries the risks of infection and bleeding.

In this regard, it is required to significantly reduce the amount of radiation exposure by using heat, instead of radiation, in cancer treatment. In addition, it is required to trace the exact location of a cancer cell (i.e., a target) using PET and then remotely heat the cancer cell instead of inserting the electrode 21 into the human body P as in RFA. In particular, whenever a patient is treated, the location of a target to be treated may be changed. Therefore, it is required to trace the location of the target in real time and treat the target immediately.

In other words, imaging diagnosis for identifying the location and size of a tumor and thermotherapy that replaces radiation therapy should be performed simultaneously. That is, it is required to reduce treatment time and the amount of radiation exposure by simultaneously performing the monitoring and thermotherapy of a target.

SUMMARY OF THE INVENTION

Aspects of the present invention provide a positron emission tomography (PET)-radiofrequency ablation (RFA) complex medical device which traces and targets the exact location of a cancer cell (i.e., a target to be treated) in real time using PET and then treats the cancer cell at the targeted location using RFA and a treatment method using the PET-RFA complex medical device.

Aspects of the present invention also provide a PET-RFA complex medical device in which an RFA structure for focusing heat on a location targeted by PET and a PET detector form an ellipsoidal structure to induce better performance and a treatment method using the PET-RFA complex medical device.

However, aspects of the present invention are not restricted to the one set forth herein. The above and other aspects of the present invention will become more apparent to one of ordinary skill in the art to which the present invention pertains by referencing the detailed description of the present invention given below.

According to an aspect of the present invention, there is provided a positron emission tomography (PET)-radiofrequency ablation (RFA) complex medical device comprising: a PET module which obtains, in real time, a location of a target to be treated by scanning a patient; and an RFA module which remotely treats the target using heat by focusing the heat on the location of the target.

According to another aspect of the present invention, there is provided a PET-RFA complex medical device comprising: a PET module which obtains, in real time, a location of a target to be treated by scanning a patient; and a pair of RFA modules which are connected to the PET module with the PET module interposed therebetween, wherein the target traced by the PET module is remotely treated using heat by the RFA modules.

According to another aspect of the present invention, there is provided a treatment method comprising: obtaining a location of a target to be treated by using PET; and remotely treating the target using heat by focusing the heat on the location of the target using RFA.

The above and other features and advantages of the present invention will become more apparent by describing in detail exemplary embodiments thereof with reference to the attached drawings in which:

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION OF THE INVENTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. The same reference numbers indicate the same components throughout the specification. In the attached figures, the thickness of layers and regions is exaggerated for clarity.

Unless defined otherwise, all technical and scientific terms used herein have the same meaning as commonly understood by one of ordinary skill in the art to which this invention belongs. It is noted that the use of any and all examples, or exemplary terms provided herein is intended merely to better illuminate the invention and is not a limitation on the scope of the invention unless otherwise specified. Further, unless defined otherwise, all terms defined in generally used dictionaries may not be overly interpreted.

Hereinafter, the present invention will be described in detail with reference to the attached drawings.

Figure 1:
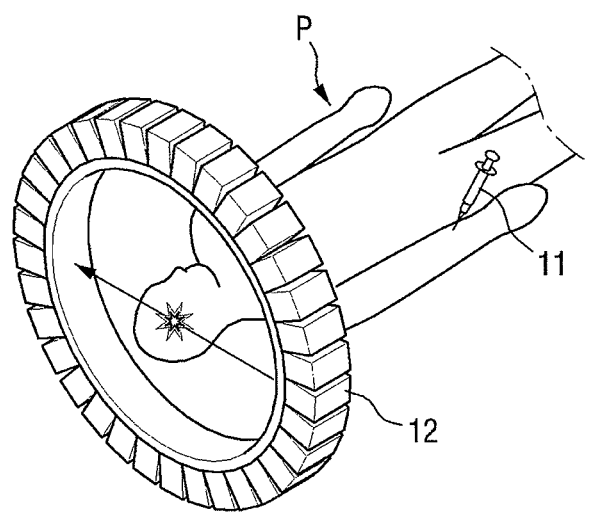
FIG. 1 is a diagram illustrating cancer detection using conventional positron emission tomography (PET)
Figure 2:
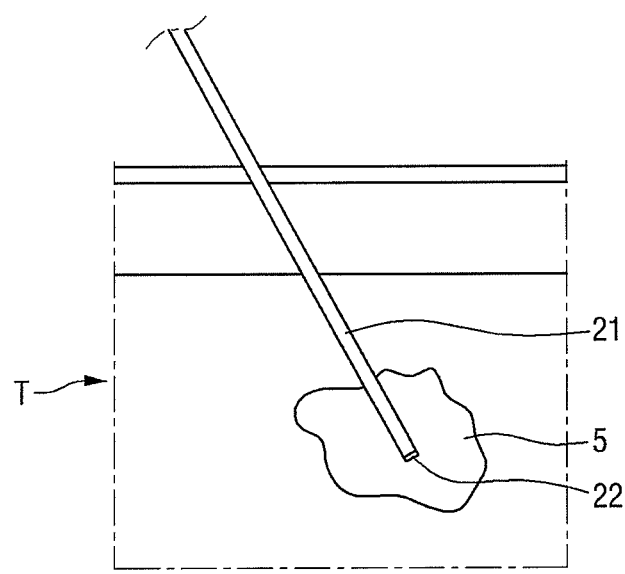
FIG. 2 is a diagram illustrating cancer treatment using conventional radiofrequency ablation (RFA)
Figure 3:
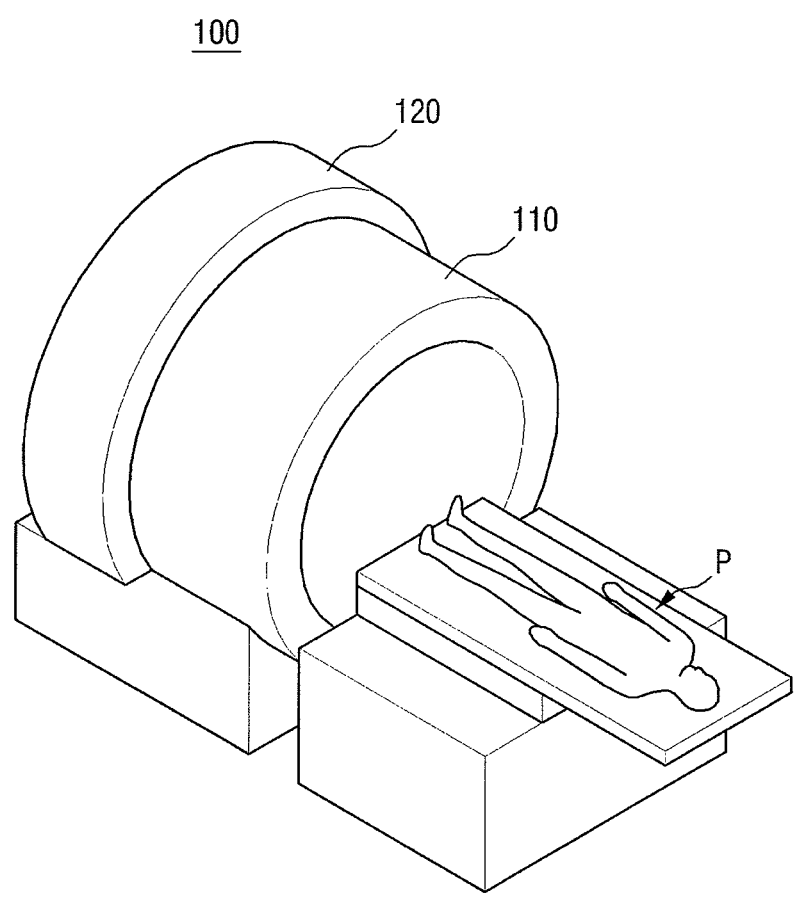
FIG. 3 is a diagram illustrating a PET-RFA complex medical device according to an embodiment of the present invention.

FIG. 3 is a diagram illustrating a positron emission tomography (PET)-radiofrequency ablation (RFA) complex medical device 100 according to an embodiment of the present invention.

Referring to FIG. 3, the PET-RFA complex medical device 100 according to the current embodiment may include a PET module 110 which obtains, in real time, the location of a target to be treated by scanning a patient and an RFA module 120 which remotely treats the target by focusing heat on the location of the target. Here, the target may mostly be a cancer cell. However, the target is not limited to the cancer cell, and it is obvious to those of ordinary skill in the art that the target is any lesion that can be remotely treated with heat.

The PET module 110 obtains the location of a target to be treated by introducing positrons into the body of a patient P. Specifically, the PET module 110 injects a tracer into the patient P using a radioactive isotope such as C-11, N-13, F-18, etc. and obtains the location of the target using positrons emitted from the radioactive isotope. For example, F-18-fluorodeoxyglucose (FDG), which is the most commonly used radiopharmaceutical, is a glucose-like substance. Therefore, if F-18-FDG is injected into the patient P, it becomes concentrated in a region (such as cancer) where glucose metabolism has been accelerated within the body of the patient P. The positrons emitted from the radioactive isotope consume all their kinetic energy for a very short time after emission and combine with neighboring electrons to disappear. Here, two annihilation radiations (gamma radiations) are emitted at an angle of 180 degrees to each other.

The cylindrical PET module 110 detects the two annihilation radiations emitted simultaneously. If an image is reconstructed using the detected radiations, how much radiopharmaceutical has been concentrated in where in the body of the patient P can be presented in a 3D tomography image. Although not illustrated in FIG. 3, the PET module 110 includes a plurality of scintillation crystals and a signal processor. The scintillation crystals may be NaI, bismuth germinate oxide (BGO), or cerium-doped lutetium oxyorthosilicate (LSO) that can be adopted by those of ordinary skill in the art. The signal processor converts light from the scintillation crystals into photoelectrons and converts the photoelectrons into an electrical signal. The electrical signal generated by the PET module 110 is input to an image processor (not shown), converted into an output image, and provided accordingly.

The RFA module 120 generates heat by focusing radiofrequency waves on the location of the target obtained by the PET module 110 and treats the target using the generated heat. Accordingly, the target is removed. That is, while an electrode is inserted into a target in conventional RFA, heat is focused on the target at a distance to treat the target in remote RFA according to the present invention. Since heat is used instead of radiation used in radiation therapy, the amount of radiation exposure can be reduced. In addition, it is possible to remove the danger and side effects of RFA in which an electrode for applying heat to a cancer cell is inserted directly into the human body.

As illustrated in FIG. 3, the PET module 110 and the RFA module 120 may form one unit in appearance. In this structure, the location information of the target is obtained in real time using the PET module 110 In addition, no electrode is inserted into the body of the patient P. Instead, the target is treated by remotely focusing heat on the target using the RFA module 120. Since the monitoring and thermotherapy of the target are performed simultaneously, the treatment time and the amount of radiation exposure can be reduced.

Figure 4:
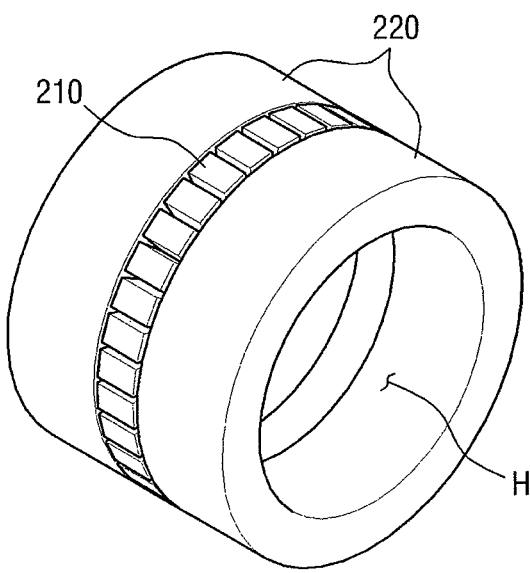
FIG. 4 is a diagram illustrating a PET-RFA complex medical device according to another embodiment of the present invention.

FIG. 4 is a diagram illustrating a PET-RFA complex medical device 200 according to another embodiment of the present invention.

Referring to FIG. 4, the PET-RFA complex medical device 200 according to the current embodiment includes a PET module 210 which obtains, in real time, the location of a target to be treated by scanning a patient and a pair of RFA modules 220 which are coupled to the PET module 210 with the PET module 210 interposed therebetween. The RFA modules 220 which focus heat on a location targeted by the PET module 210 may form a ring-shaped structure together with the PET module 210. Therefore, a target traced by the PET module 210 can be effectively and remotely treated with heat by using the RFA modules 220. Accordingly, whenever a patient is treated, a change in the location of the target can be identified in real time using the device 200 that combines the PET module 210 and the RFA modules 220, and the target at the changed location can be treated with heat immediately. That is, the integration of the PET module 210 and the RFA modules 220 makes it possible to effectively conduct diagnosis and treatment using one device 200 in a short period of time. Here, the PET module 210 may obtain the location of a target by irradiating positrons, and the pair of RFA modules 220 may generate heat by focusing radiofrequency waves on the location of the target and remove the target using the generated heat as described above.

Since the PET module 210 and the pair of RFA modules 220 are homocentric, accurate detecting and targeting of a target are possible. In addition, the PET module 210 and the pair of RFA modules 220 may each have a cylindrical shape to form one cylindrical unit. Otherwise, the PET module 210 and the pair of RFA modules 220 may form one unit having a polyhedral shape such as a quadrilateral, a hexagon or an octagon as obvious to those of ordinary skill in the art.

Each of the PET module 210 and the pair of RFA modules 220 may include a hole H to accommodate a patient. The patient may be placed inside the PET module 210 and the pair of RFA modules 220 through the hole H. Therefore, the location of cancer (i.e., a target) can be targeted according to a line of response (LOR) of the cancer, and the cancer at the targeted location can be treated with heat. In addition, since the target is treated while tracing a change in the location of the target due to the movement of the patient or other factors, the efficiency of the treatment can be increased. That is, LOR information of a target to be treated is obtained in real time using the PET module 210, and the target is treated using the pair of RFA modules 220 focused on the LOR. Therefore, treatment time can be reduced. In addition, since the PET module 210 does not need to obtain an image, LOR information can be obtained even if a smaller amount of radiotracer is injected than in case of PET imaging. This can reduce the amount of radiation exposure.

Therefore, the pair of RFA modules 210 may generate radiofrequency waves based on location information of a target obtained by the PET module 210 and remove the target using the generated heat. Since the monitoring of a target using the PET module 210 and the thermotherapy of the target using the RFA modules 220 are performed simultaneously, both the treatment time and the amount of radiation exposure can be reduced.

Figure 5:
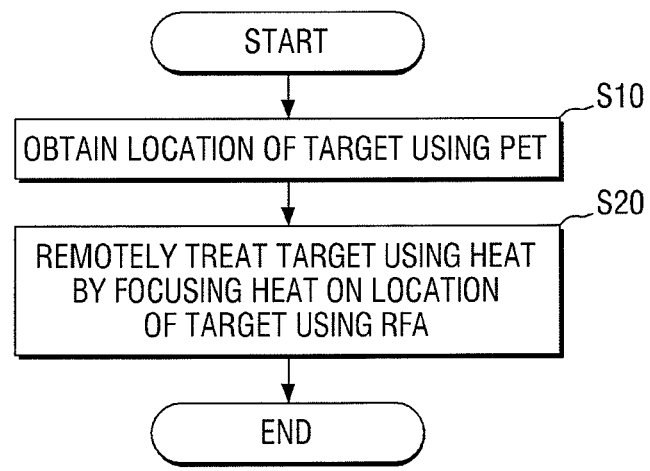
FIG. 5 is a flowchart illustrating a treatment method using a PET-RFA complex medical device according to an embodiment of the present invention.

FIG. 5 is a flowchart illustrating a treatment method using a PET-RFA complex medical device according to an embodiment of the present invention.

Referring to FIG. 5, the treatment method using a PET-RFA complex medical device according to the current embodiment includes obtaining the location of a target to be treated using PET (operation S10) and remotely treating the target using heat by focusing the heat on the location of the target using RFA (operation S20).

Specifically, location information of a target is obtained in real time using PET, and the target is treated with heat using remote RFA which focuses heat on the target at a distance instead of inserting an electrode into the target. Since the monitoring and thermotherapy of a target are performed simultaneously using a combination of PET and RFA technologies, both the treatment time and the amount of radiation exposure can be reduced.

Therefore, the present invention can significantly reduce the amount of radiation exposure and treatment time compared with conventional radiation therapy and remove side effects caused by a large amount of radiation exposure. These advantages make it possible to preoccupy the large international radiation therapy market.

According to the present invention, since RFA uses heat instead of radiation used in radiation therapy, the amount of radiation exposure can be significantly reduced.

In addition, it is possible to obtain information about a cancer cell even if a smaller amount of radiotracer is injected than in case of PET imaging. This also reduces the amount of radiation exposure.

Further, an LOR of a target to be treated can be obtained in real time, and the target can be treated using RFA focused in advance on the LOR. That is, since it is possible to treat the target while tracing the movement of the target, treatment time can be reduced.

Lastly, remote thermotherapy performed herein can remove the danger and side effects of conventional RFA in which an electrode is inserted into the human body.

In concluding the detailed description, those skilled in the art will appreciate that many variations and modifications can be made to the preferred embodiments without substantially departing from the principles of the present invention. Therefore, the disclosed preferred embodiments of the invention are used in a generic and descriptive sense only and not for purposes of limitation.

What is claimed is:

1. A positron emission tomography (PET)-radiofrequency ablation (RFA) complex medical device comprising: a PET module which obtains, in real time, a location of a target to be treated by scanning a patient; and a pair of RFA modules that are connected to the PET module with the PET module interposed therebetween, wherein the PET module and the pair of RFA modules are homocentric, wherein the RFA modules are configured to remotely treat the located target by generating heat by focusing radiofrequency waves, and wherein the PET module and the pair of RFA modules are configured to simultaneously perform the scanning of the patient and the focusing of the target.

2. The medical device of claim 1, wherein the target is a cancer cell.

3. The medical device of claim 2, wherein the PET module obtains the location of the target by irradiating positrons.

4. The medical device of claim 1, wherein the PET module and the pair of RFA modules form one unit in appearance.

5. The medical device of claim 1, wherein the PET module and the pair of RFA modules each have a cylindrical shape to form one cylindrical unit.

6. The medical device of claim 1, wherein each of the PET module and the pair of RFA modules comprises a hole to accommodate the patient.

7. The medical device of claim 1, wherein the PET module obtains the location of the target by irradiating positrons.

* * * * *